United States Patent [19]

Hoeger et al.

[11] Patent Number: 5,750,499

[45] Date of Patent: May 12, 1998

[54] RECEPTOR-SELECTIVE SOMATOSTATIN ANALOGS

[75] Inventors: Carl A. Hoeger, San Marcos; Jean E. F. Rivier, La Jolla, both of Calif.

[73] Assignee: The Salk Institute for Biological Studies, San Diego, Calif.

[21] Appl. No.: 544,805

[22] Filed: Oct. 18, 1995

[51] Int. Cl.$^6$ .......................... A61K 38/12; A61K 38/31; C07K 14/655

[52] U.S. Cl. ...................... 514/9; 514/11; 514/13; 514/14; 530/311; 530/327

[58] Field of Search .................... 514/14, 13, 9, 514/11; 530/311, 327

[56] References Cited

U.S. PATENT DOCUMENTS

| | | | |
|---|---|---|---|
| 4,428,942 | 1/1984 | Rivier et al. | 424/177 |
| 4,581,169 | 4/1986 | Nestor et al. | 260/112.5 |
| 4,816,438 | 3/1989 | Spiess et al. | 514/11 |
| 5,436,155 | 7/1995 | Bell et al. | 435/252.3 |

OTHER PUBLICATIONS

Hirst et al., 'Structure–activity studies with somatostatin: role of lysine in position 4 and 9 for gastric activity'. Regulatory Peptides, vol. 8, pp. 267–271, 1984.

*Primary Examiner*—Cecilia J. Tsang
*Assistant Examiner*—Anism Gupta
*Attorney, Agent, or Firm*—Fitch, Even, Tabin & Flannery

[57] ABSTRACT

Analogs of SRIF which are selective for SSTR1 in contrast to the other cloned SRIF receptors. These analogs are useful in determining the tissue and cellular expression of the receptor SSTR1 and its biological role in the endocrine, exocrine and nervous system, as well as in regulating tumor growth. SRIF analog peptides, such as des-AA$^{1,2,5}$[D-Trp$^8$, IAmp$^9$]-SRIF inhibit the binding of [$^{125}$I-Tyr$^{11}$]SRIF to the cloned human receptor SSTR1 but do not bind to mouse SSTR2 and SSTR3, human SSTR4 or rat SSTR5. By incorporating an iodinated tyrosine in position-2 in these selective SRIF analogs, a labelled compound useful in drug-screening methods is provided.

21 Claims, No Drawings

RECEPTOR-SELECTIVE SOMATOSTATIN ANALOGS

This invention is directed to peptides related to somatostatin and to methods for pharmaceutical treatment of mammals using such peptides. More specifically, the invention relates to shortened somatostatin analogs, to pharmaceutical compositions containing such peptides, to methods of diagnosis and treatment of mammals using such peptides and to drug screening methods using such peptides.

BACKGROUND OF THE INVENTION

The cyclic tetradecapeptide somatostatin-14 (SRIF) was originally isolated from the hypothalamus and characterized as a physiological inhibitor of growth hormone release from the anterior pituitary. It was characterized by Guillemin et al. and is described in U.S. Pat. No. 3,904,594 (Sep. 9, 1975). This tetradecapeptide has a bridging or cyclizing bond between the sulfhydryl groups of the two cysteinyl amino acid residues in the 3- and 14-positions. SRIF was found to also regulate insulin, glucagon and amylase secretion from the pancreas, and gastric acid release in the stomach. SRIF is also expressed in intrahypothalamic regions of the brain and has a role in the regulation of locomotor activity and cognitive functions. SRIF is localized throughout the central nervous system, where it acts as a neurotransmitter. In the central nervous system, SRIF has been shown to both positively and negatively regulate neuronal firing, to affect the release of other neurotransmitters, and to modulate motor activity and cognitive processes.

Somatostatin and many analogs of somatostatin exhibit activity in respect to the inhibition of growth hormone (GH) secretion from cultured, dispersed rat anterior pituitary cells in vitro; they also inhibit GH, insulin and glucagon secretion in vivo in the rat and in other mammals. One such analog is [D-Trp$^8$]-SRIF which has the amino acid sequence: (cyclo 3-14)H-Ala-Gly-Cys-Lys-Asn-Phe-Phe-D-Trp-Lys-Thr-Phe-Thr-Ser-Cys-OH, which is disclosed in U.S. Pat. No. 4,372,884 (Feb. 8, 1983). Somatostatin has also been found to inhibit the secretion of gastrin and secretin by acting directly upon the secretory elements of the stomach and pancreas, respectively, and somatostatin is being sold commercially in Europe for the treatment of ulcer patients. The powerful inhibitory effects of somatostatin on the secretion not only of GH but also of insulin and glucagon have led to studies of a possible role of somatostatin in the management or treatment of juvenile diabetes and have proved useful in studying the physiological and pathological effects of these hormones on human metabolism.

L. Pradayrol, et al. in *FEBS Letters* 109, January 1980, pages 55–58, reported the isolation and characterization of somatostatin-28 (SRIF-28) from porcine upper small intestine. SRIF-28 is an N-terminally extended version of SRIF which has an additional 14 amino acid residues and which shows some increased potency when administered in vivo.

SRIF affects multiple cellular processes. Studies have shown that SRIF is an inhibitory regulator of adenylyl cyclase in different tissues. SRIF also regulates the conductance of ionic channels, including both $K^+$ and $Ca^{2+}$ channels. These actions of SRIF are mediated via pertussis toxin-sensitive guanine nucleotide-binding proteins. SRIF also regulates the activity of tyrosine phosphatases, the $Na^+/H^+$ antiport and cellular proliferation through pertussis toxin-insensitive mechanisms.

SRIF induces its biological effects by interacting with a family of membrane-bound structurally similar receptors. Five SRIF receptors have fairly recently been cloned and are referred to as SSTR1–5. Human SSTR1, mouse SSTR2 and mouse SSTR3 are described in Raynor et al., *Molecular Pharmacology*, 43, 838–844 (1993), the disclosure of which is incorporated herein by reference. Human SSTR1, 2 and 3 are disclosed in U.S. Pat. No. 5,436,155 (Jul. 25, 1995), the disclosure of which is incorporated herein by reference. All five receptors, including the human SSTR4 and the rat SSTR5, bind SRIF and SRIF-28 with high affinity. Selective agonists at SSTR2 and SSTR5 have been identified and used to reveal distinct functions of these receptors. SSTR2 is believed to mediate the inhibition of growth hormone, glucagon and gastric acid secretion. In contrast, SSTR5 appears to be primarily involved in the control of insulin and amylase release. SSTR3 is believed to mediate inhibition of gastric smooth muscle contraction by SRIF. These findings indicate that different receptor subtypes appear to mediate distinct functions of SRIF in the body.

SRIF has also now been found to inhibit tumor cell proliferation, and a cyclic SRIF analog, termed SMS-201-995, i.e. D-Phe-Cys-Phe-D-Trp-Lys-Thr-Cys-Thr-ol is being used clinically to inhibit tumor growth and as a diagnostic agent to detect SRIF receptors expressed in cancers. SMS-201-995 and other clinically used SRIF analogs interact significantly with three of the receptor subtypes, i.e. SSTR2, SSTR3 and SSTR5. SSTR2 and SSTR5 have recently been reported to mediate antiproliferative effects of SRIF on tumor cell growth; therefore, they may mediate the clinical effects of SMS-201-955 in humans.

SSTR1 was the first SRIF receptor cloned. It has high affinity for SRIF and SRIF-28, but it has very low affinity for most synthetic analogs of SRIF. SSTR1 mRNA is expressed in the central nervous system as well as in a number of endocrine and exocrine organs, and SSTR1 mRNA is particularly high in a number of tumors. The cloned SSTR1 has been reported to mediate antiproliferative effects of SRIF possibly by modulating the activity of a Na+/H+ ion exchanger or through the stimulation of a tyrosine phosphatase. SSTR1 is therefore considered to be an important target both for the physiological actions of SRIF and for the therapeutic actions of SRIF analogs to inhibit tumor cell growth.

The search has continued for somatostatin analogs which are more potent than somatostatin and/or exhibit dissociated inhibitory functions, and particularly for analogs which are selective for SSTR1. However, no ligand has been available that selectively binds to SSTR1, and efforts to determine the precise localization of SSTR1 in the body and to identify its biological actions have been hindered by the lack of selective SSTR1 ligands.

SUMMARY OF THE INVENTION

Certain modifications have now been discovered which are effective to create analogs of SRIF that are selective for SSTR1 in contrast to the other cloned SRIF receptors. SRIF agonist peptides have been created that bind specifically to cloned SSTR1, and analogs of these peptides can be iodinated while retaining their desirable biological properties. These novel peptides are useful in determining the tissue and cellular expression of the receptor SSTR1 and its biological role in the endocrine, exocrine and nervous system, as well as in regulating tumor growth and certain other pharmacological functions for which SRIF has previously been used without the accompanying side effects heretofore characteristic of administering SRIF.

The SRIF analog peptides of the invention inhibit the binding of [$^{125}$I-Tyr$^{11}$]SRIF to the cloned human receptor SSTR1, but they do not bind to mouse SSTR2 and SSTR3, human SSTR4 or rat SSTR5. Additional of these SRIF analogs which incorporate an iodinated tyrosine in position-2 also do not bind to SSTR2–5 but still bind potently and saturably to SSTR1. The binding of these SRIF analogs to SSTR1 expressed in COS-7 cells is reduced by GTPgS and pertussis toxin treatment, whereas the binding of [$^{125}$I-Tyr$^{11}$]SRIF to SSTR1 (to which it also binds strongly) is not affected by these treatments, indicating that these SRIF analogs bind to SSTR1 in a different manner than the native peptide SRIF.

Many of these SRIF analogs not only selectively bind to SSTR1, but they bind thereto with high affinity. By selectively binding is meant that they exhibit a $K_d$ or an $IC_{50}$ with SSTR1 of about one-tenth or less of that with respect to at least 3 of the other SRIF receptors. They are useful in localizing such receptor in the body and in diagnosing for tumors which express the SSTR1 receptor. Moreover, they are particularly useful in combatting tumor growth which is mediated by the SSTR1 receptors because such can be carried out without the side effects that would otherwise accompany administration of currently available SRIF analogs which interact with a plurality of SRIF receptors. Certain of these SRIF analogs can be readily labelled and used in effective drug screening methods. They can also be used in the selective purification of SSTR1 receptors that can then be employed in drug-screening tests.

DETAILED DESCRIPTION OF THE PREFERRED EMBODIMENTS

Unless defined otherwise, all technical and scientific terms used herein have the same meaning as is commonly understood by one of skill in the art to which this invention belongs. The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations to identify the alpha-amino acid residues, and where the amino acid residue has isomeric forms, it is the L-form of the amino acid that is represented unless otherwise expressly indicated, e.g. Ser=L-serine. By D,L is meant a mixture of the D- and L-isomers of a particular α-amino acid.

SRIF analog peptides are provided having a selective affinity for the SRIF receptor SSTR1; the preferred analogs also have a high affinity for SSTR1, i.e. equal to a $K_d$ of about 10 nanomolar or less. These peptides broadly encompass known analogs of SRIF or obvious variations thereof which have a D-isomer, preferably an aromatic D-isomer, and more preferably D-Trp or D-Nal, in the position corresponding to the 8-position of the native peptide and an aminomethylPhe residue, which may be alkylated, in the adjacent position that corresponds to the 9-position of the native peptide. So long as the basic molecule exhibits SRIF properties by binding to SRIF receptors, insertion of this combination of residues in the corresponding 8- and 9-positions will create a molecule which is highly selective for the SSTR1 receptor. Preferably the 5-position residue is also deleted to increase binding affinity to SSTR1. Since the characterization of SRIF, a large number of SRIF analogs have been synthesized having increased potency in some respect, which can be rendered selective for the SSTR1 receptor by the incorporation of the modification of the present invention, and the following U.S. Pat. Nos. are illustrative of such SRIF analogs, the disclosures of which are incorporated here in by reference: Re. 30,548; 4,133, 782; 4,211,693; 4,316,891; 4,372,884; 4,393,050; 4,061, 608; 4,081,433; 4,182,707; 4,190,575; 5,185,010; 4,215, 039; 4,230,617; 4,238,481; 4,253,998; 4,282,143; 4,328, 214; 4,358,439; 4,209,441; 4,210,636; 4,316,890; and 5,073,541.

Examples of some representative peptides exhibiting desired features of the invention include those having the following amino acid sequence, which is based upon a numbering system consistent with the 14-residue sequence of native mammalian SRIF:

(cyclo 3-14)Xaa$_1$-Xaa$_2$-Cys-Lys-Xaa$_5$-Phe-Phe-D-Xaa$_8$-Xaa$_9$-Thr-Phe-Thr-Xaa$_{13}$-Cys wherein Xaa$_1$ is des-Xaa or Ala; Xaa$_2$ is Tyr, D-Tyr or des-Xaa or Gly; Xaa$_5$ is des-Xaa or Asn; D-Xaa$_8$ is a D-amino acid; Xaa$_9$ is an aminomethyl Phe; and Xaa$_{13}$ is Ser or D-Ser. Xaa$_5$ is preferably des-Xaa. D-Xaa$_8$ should be aromatic an d may be D-Trp or a substituted D-Trp, or an equivalent residue such as D-Nal. Xaa$_9$ includes a Phe residue that has an aminomethyl substitution on the phenyl ring, i.e. Amp, preferably in the 3- or 4-position on the ring, and most preferably Xaa$_9$ includes (C)4Amp where C is hydrogen or lower alkyl(C$_1$ to C$_5$) group. More preferably C is methyl, ethyl, isopropyl or isobutyl, and most preferably C is isopropyl.

A preferred subgenus of SRIF agonists has the amino acid sequence:

(cyclo 3-14)Xaa$_1$-Xaa$_2$-Cys-Lys-Xaa$_5$-Phe-Phe-D-Xaa$_8$-Xaa$_9$-Thr-Phe-Thr-Xaa$_{13}$-Cys wherein Xaa$_1$ is des-Xaa; Xaa$_2$ is Tyr, D-Tyr or des-Xaa; Xaa$_5$ is des-Xaa; D-Xaa$_8$ is either D-Trp or a substituted D-Ala wherein one hydrogen on the β-carbon is replaced by:

(a) a carbocyclic aryl-containing radical selected from the group consisting of phenyl substituted with three or more straight chain lower alkyl groups, naphthyl, pyridyl, anthryl, fluorenyl, phenanthryl, biphenylyl and benzhydryl; or (b) a saturated carbocyclic radical selected from the group consisting of cycloalkyl substituted with three or more straight chain lower alkyl groups, perhydronaphthyl, perhydrobiphenylyl, perhydro-2,2-diphenylmethyl, and adamantyl;

Xaa$_9$ is an aminomethyl Phe that is optionally (C$_1$ to C$_5$)alkylated; and Xaa$_{13}$ is Ser or D-Ser.

Another preferred subgenus of SRIF agonist peptides has the amino acid sequence:

(cyclo 3-14)Xaa$_1$-Xaa$_2$-Cys-Lys-Xaa$_5$-Phe-Phe-D-Xaa$_8$-Xaa$_9$-Thr-Phe-Thr-Xaa$_{13}$-Cys wherein Xaa$_1$ is des-Xaa; Xaa$_2$ is Tyr, D-Tyr or des-Xaa; Xaa$_5$ is des-Xaa; D-Xaa$_8$ is either D-Trp or a D-Ala wherein one hydrogen on the β-carbon is replaced by:

(a) a carbocyclic aryl-containing radical selected from the group consisting of phenyl substituted with three or more straight chain lower alkyl groups, naphthyl, pyridyl, anthryl, fluorenyl, phenanthryl, biphenylyl and benzhydryl; or (b) a saturated carbocyclic radical selected from the group consisting of cycloalkyl substituted with three or more straight chain lower alkyl groups, perhydronaphthyl, perhydrobiphenylyl, perhydro-2,2-diphenylmethyl, and adamantyl.

Xaa$_9$ is a (C$_3$ or C$_4$)alkylated aminomethyl Phe; and Xaa$_{13}$ is Ser or D-Ser.

An additional preferred subgenus of SRIF agonist peptides has the amino acid sequence:

(cyclo 3-14)Xaa$_1$-Xaa$_2$-Cys-Lys-Xaa$_5$-Phe-Phe-D-Xaa$_8$-Xaa9-Thr-Phe-Thr-Xaa$_{13}$-Cys wherein Xaa$_1$ is des-Xaa; Xaa$_2$ is Tyr, D-Tyr or des-Xaa; Xaa$_5$ is des-Xaa; D-Xaa$_8$ is (A)D-Trp where A is H, F, Cl or Br, or (B)D-Ala or (B)D,L-Ala where B is naphthyl, pyridyl, fluorenyl, adamantyl, anthryl, biphenyl, tri(lower alkyl)phenyl, pentamethylphenyl, phenanthryl, trialkylcyclohexyl, perhydronaphthyl or perhydrobiphenyl; $Xaa_9$ is a ($C_3$ or $C_4$)alkylated aminomethyl Phe; and Xaa13 is Ser or D-Ser.

Still another preferred subgenus of SRIF agonist peptides has the amino acid sequence:
(cyclo 3-14)$Xaa_1$-$Xaa_2$-Cys-Lys-$Xaa_5$-Phe-Phe-D-$Xaa_8$-$Xaa_9$-Thr-Phe-Thr-$Xaa_{13}$-Cys wherein $Xaa_1$ is des-Xaa; $Xaa_2$ is Tyr, D-Tyr or des-Xaa; $Xaa_5$ is des-Xaa; D-$Xaa_8$ is D-Trp, D-1Nal, D-Me5-Phe, D-TMP, D-BIA, D-TBA,-D-anthryl-Ala, D-fluorenyl-Ala or D-adamantyl-Ala; $Xaa_9$ is isopropyl-4-aminomethyl Phe; and $Xaa_{13}$ is Ser or D-Ser.

By β-D-Nal is meant the D-isomer of alanine which is substituted by naphthyl on the β-carbon atom; it is alternatively referred to as 3-D-Nal. Preferably 3-D-2Nal is employed wherein the attachment to naphthalene is at the 2-position on the ring structure; however, 3-D-1Nal may also be used. Pal represents alanine which is substituted by pyridyl on the β-carbon atom; preferably the linkage is to the 3-position on the pyridine ring. When substituted D-Trp is employed, single substitutions for hydrogen are preferably made in either the 5- or 6-position, which are selected from chloro, fluoro, bromo and nitro, with chloro, fluoro and nitro being preferred. Alternatively, the indole nitrogen may be acylated with formyl ($N^{in}$For- or 1For-). By Amp is meant (aminomethyl)phenylalanine; unless otherwise specified, the methyl group with its amino substitution should be understood to be in the 4- or para-position on the phenyl ring. By IAmp is meant (N-isopropyl-aminomethyl) phenylalanine, where the amino group is alkylated with an isopropyl group. By D-Me5Phe is meant 3-(2,3,4,5,6-pentamethylphenyl)-D-Ala. By D-TMP is meant 3-(2,4,6-trimethylphenyl)-D-Ala. By D-BIA is meant 3-(benzimidazol-2-yl)-D-Ala. By D-TBA is meant 3-(4,5,6,7-tetrahydrobenzimidazol-2-yl)-D-Ala.

As used herein, the term "lower alkyl" refers to a straight or branched chain, saturated hydrocarbon group having from 1 to 5 carbon atoms such as, for example, methyl, ethyl, n-propyl, isopropyl, n-butyl, isobutyl, sec-butyl, tert-butyl, isopentyl and n-pentyl; the term "cycloalkyl group" refers to a cyclic saturated hydrocarbon group having from 4 to 6 carbon atoms, e.g. cyclobutyl, cyclopentyl and cyclohexyl. As used herein, "naphthyl" is inclusive of 1- and 2-naphthyl; "anthryl" is inclusive of 1-, 2- and 9-anthryl; "fluorenyl" is inclusive of 2-,3-,4- and 9-fluorenyl; "phenanthryl" is inclusive of 2-,3- and 9-phenanthryl; and "adamantyl" is inclusive of 1- and 2-adamantyl.

Although SSTR1 was the first somatostatin receptor cloned, identification of its biological and pharmacological properties has lagged behind the other SRIF receptors because of the lack of ligands which are significantly selective for SSTR1. The peptides of the invention are believed to be the first truly SSTR1-selective ligands, which will accordingly be most useful in determining the functional roles of this receptor and in selectively activating only this SRIF receptor and not the others.

Selectivity for binding of the peptides of the invention to SSTR1 was demonstrated by testing their interaction with the five different cloned SRIF receptors. Recombinant cells expressing the receptor may be washed and homogenized to prepare a crude protein homogenate in a suitable buffer as known in the art. In a typical assay, an amount of protein from the cell homogenate is placed into a small volume of an appropriate assay buffer at an appropriate pH. Candidate substances, such as potential agonists and antagonists, are added to the admixture in convenient concentrations and the interaction between the candidate substance and the receptor polypeptide is monitored. The peptides of the invention bound substantially only to SSTR1, and their binding was of high affinity.

Receptor binding assays were performed on cloned SRIF receptors as generally set forth in Raynor et al. supra to generate $K_d$ values which are indicative of the concentration of a ligand necessary to occupy one-half (50%) of the binding sites on a selected amount of a receptor or the like. Alternatively, $IC_{50}$ values indicative of the concentration of a competitive ligand necessary to displace a saturation concentration of a target ligand being measured from 50% of binding sites can also be calculated in such competitive assays. The peptide des-$AA^{1,2,5}$-[D-$Trp^8$, $IAmp^9$]SRIF inhibits the binding of [$^{125}$I-$Tyr^{11}$]SRIF to the cloned human SSTR1 with an $IC_{50}$ of 1.8±0.7 nM. This SRIF analog peptide does not bind to mouse SSTR2, mouse SSTR3, human SSTR4 or rat SSTR5 at concentrations below 100 nM.

An analog of des-$AA^{1,2,5}$-[D-$Trp^8$, $IAmp^9$]SRIF having a tyrosine residue in position-2 was iodinated and tested for binding to the cloned SRIF receptors. $^{125}$I-$Tyr^2$-des-$AA^{1,5}$-[D-$Trp^8$, $IAmp^9$]SRIF likewise did not bind to SSTR2-5, but it bound potently and saturably to SSTR1 with a Kd of 0.5±0.1 nM and a $B_{max}$ of 226±56 fmol/mg protein. The $B_{max}$ value represents the highest number of specific sites which can be occupied at a given time, i.e. the saturation point. The binding of $^{125}$I-$Tyr^2$-des-$AA^{1,5}$-[D-$Trp^8$, $IAmp^9$]SRIF to SSTR1 was potently inhibited by SRIF, [D-$Trp^8$]SRIF and SRIF-28, with $IC_{50}$ values of 0.8±0.4, 0.2±0.1 and 0.7±0.2 nM, respectively. Furthermore the SRIF analog des-$AA^{1,2,5}$-[D-$Trp^8$, $IAmp^9$, D-$Ser^{13}$]SRIF potently bound to SSTR1 with an $IC_{50}$ value of 5.3±0.8 nM compared to $^{125}$I-$Tyr^2$-des-$AA^{1,5}$-[D-$Trp^8$, $IAmp^9$]SRIF. In contrast, SRIF analogs that selectively bind to SSTR2 and SSTR5 were impotent in displacing $^{125}$I-$Tyr^2$-des-$AA^{1,5}$-[D-$Trp^8$, $IAmp^9$]SRIF from SSTR1. The binding of $^{125}$I-$Tyr^2$-des-$AA^{1,5}$-[D-$Trp^8$, $IAmp^9$]SRIF to SSTR1 expressed in COS-7 cells was reduced by GTPgS and pertussis toxin treatment; in contrast, the binding of [$^{125}$I-$Tyr^{11}$]SRIF to SSTR1 was not affected by these treatments. These findings indicate that des-$AA^{1,2,5}$-[D-$Trp^8$, $IAmp^9$]SRIF and $^{125}$I-$Tyr^2$-des-$AA^{1,5}$-[D-$Trp^8$, $IAmp^9$]SRIF may bind to SSTR1 in a different manner than the native peptide SRIF. des-$AA^{1,2,5}$-[D-$Trp^8$, $IAmp^9$]SRIF and the other SRIF analogs that selectively bind to SSTR1 with high affinity are found to activate the SSTR1 receptor. Accordingly, these SRIF analogs are considered to be useful in combatting tumor growth which is mediated by the receptor without activating the other SRIF receptors.

Although the binding of the SRIF analogs of the invention to SSTR1 is potently inhibited by native SRIF and by SRIF-28, it is not inhibited by many other synthetic SRIF analogs. Moreover, the lack of binding of the peptides of the invention to SSTR4 is of particular interest because SSTR1 and SSTR4 have approximately 68% amino acid sequence identity, which constitutes higher sequence similarity than for any other two SRIF receptors. Furthermore, SSTR1 and SSTR4 both exhibit very low affinity for a large number of other synthetic analogs of SRIF which bind potently to SSTR2, SSTR3 and SSTR5. The high amino acid sequence similarity and similar ligand binding characteristics would usually have predicted that these two SRIF receptors would share some common structural similarities in ligand-binding domains; however, the fact that the peptides of the invention selectively bind only to SSTR1 indicates that there may be considerable differences in ligand-binding properties between these two otherwise structurally similar receptors.

SSTR1 has been reported to couple to a tyrosine phosphatase, and stimulation of this enzyme is believed to mediate anti-proliferative effects of SRIF via activation of this receptor. SSTR1 mRNA has been detected in a number of tumors. The ability of SSTR1 to mediate anti-proliferative effects of SRIF renders SSTR1-selective SRIF agonists effective as therapeutic treatment agents for treating those cancers wherein the malignant tissues express this receptor.

A particularly important advantage of SSTR1-selective agonists as anti-cancer agents may be their continued effectiveness after prolonged use. Continuous use of SMS-201-995 in the treatment of tumors is considered to be hindered by rapid desensitization of SSTR2, SSTR3 and SSTR5, the receptors this peptide can interact with; in fact, all 3 of these receptors have been reported to rapidly desensitize. In contrast, studies suggest that SSTR1 may be more resistant to agonist-induced regulation than the other receptors. As a result, the SSTR1-selective peptide agonists of the invention are considered to have prolonged anti-proliferative actions and should therefore exhibit improved effectiveness in treating cancers, compared to the commercially available SRIF analogs presently used as anti-cancer agents.

Furthermore, an analog of SMS-201-995 has recently been employed to detect human tumors having high expression of SRIF receptors through the use of positron-emission tomography. This SRIF analog does not distinguish among SSTR2, SSTR3 or SSTR5, and it is unlikely to be able to detect SSTR1 expression. Labelled SRIF analogs of the present invention can be employed for similar purposes and are considered to be specifically useful in identifying tumors expressing SSTR1, which tumors would then be therapeutic targets for treatment with SSTR1-selective ligands.

While SSTR1 has the typical structure of other G protein-linked receptors, controversy exists over whether this receptor truly associates with G proteins and effectively couples to adenylyl cyclase. Some investigators have reported that SRIF binding to this receptor is not affected by GTP analogs or pertussis toxin and does not effectively couple to adenylyl cyclase, whereas others have reported opposite findings. Furthermore, some investigators have failed to show GTP analog regulation of agonist binding to the receptor but have found that receptor mediates the inhibition of cAMP formation by SRIF; however, this may have been a function of the particular cell systems that were used.

Previous studies have now been confirmed that the binding of [$^{125}$I-Tyr$^{11}$]SRIF to SSTR1 was not significantly effected by GTP analogs nor pertussis toxin treatment. In contrast, the binding of the radiolabelled SRIF analogs of the present invention is reduced by GTPgS and the effects of GTPgS are diminished by pertussis toxin treatment. Because pertussis toxin treatment abolished the GTPgS regulation of binding, SSTR1 appears to be able to associate with $G_{ia}$ and/or $G_{oa}$ so that the SRIF analogs of the present invention will be agonists at this receptor. The regulation of the binding of the present analogs to SSTR1 by GTPgS and effect of pertussis toxin, compared to the lack of effect of these agents on SRIF binding to this receptor, suggest that SRIF and the present analogs may induce different conformational changes in SSTR1. As such, the SRIF analogs of the present invention are believed to cause an effective association of the receptor with G proteins, while SRIF may be less effective in inducing such coupling. These results imply that SRIF interacts with SSTR1 in a fundamentally distinct manner from that of the SRIF analogs of the present invention. Some results also suggest that the SRIF analogs of the present invention are able to induce responses in cells expressing SSTR1 that even SRIF is incapable of producing.

The SRIF analogs of the present invention are the first selective agonists at SSTR1 and are useful in combatting cancers which express SSTR1. They are also considered to be most useful in localizing cells and tissues expressing this receptor in the brain and in the endocrine and exocrine systems and in identifying selective functions of this receptor in body. They are further useful in selectively carrying out certain of the pharmacological effects mediated by SSTR1 for which SRIF has been found useful over the past 2 decades.

Labelled SRIF analogs of the invention are also considered to be useful in drug-screening assays to screen for new effective peptide and nonpeptide agents that will bind with high affinity to SSTR1 and which may be either highly effective agonists or antagonists. Having a known ligand for the receptor SSTR1, one can obtain a baseline activity for the recombinantly produced receptor. Then, to test for inhibitors or modifiers, i.e. antagonists of the receptor function, one can incorporate into a test mixture a candidate substance whose effect on the receptor is to be tested. By comparing reactions which are carried out in the presence or absence of the candidate substance, one can then obtain information regarding the effect of the candidate substance on the normal function of the receptor.

The peptides of the present invention can be synthesized by classical solution synthesis, but they are preferably synthesized by solid-phase technique. A chloromethylated resin or a hydroxymethylated resin is preferably used. For example, these peptides having a free carboxyl C-terminus are preferably synthesized as taught in U.S. Pat. No. 4,816,438 issued Mar. 28, 1989, the disclosure of which is incorporated herein by reference. Solid-phase synthesis is conducted in a manner to stepwise add amino acids in the chain beginning at the C-terminus in the manner set forth in that U.S. patent. Side-chain protecting groups, which are well known in the art, are preferably included as a part of any amino acid which has a particularly reactive side chain, and optionally may be used in the case of others such as Trp, when such amino acids are coupled onto the chain being built upon the resin. Such synthesis provides the fully protected intermediate peptidoresin.

Chemical intermediates used to synthesize certain preferred SRIF analogs generally in accordance with the invention may be represented by the formula:

$X^1$-Xaa$_2$($X^2$)-Cys($X^3$)-Lys($X^4$)-Phe-Phe-D-Xaa$_8$($X^5$)-Xaa$_9$ 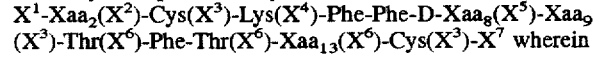
($X^3$)-Thr($X^6$)-Phe-Thr($X^6$)-Xaa$_{13}$($X^6$)-Cys($X^3$)-$X^7$ wherein $X^1$ is an α-amino protecting group of the type known to be useful in the art in the stepwise synthesis of polypeptides. When G in the desired peptide composition is a particular acyl group, it may be appropriate to employ such group as the protecting group. Among the classes of α-amino protecting groups covered by $X^1$ are (1) acyl-type protecting groups, such as formyl(For), trifluoroacetyl, phthalyl, p-toluene-sulfonyl(Tos), benzoyl(Bz), benzenesulfonyl, dithiasuccinoyl(Dts) o-nitrophenylsulfenyl(Nps), tritylsulfenyl, o-nitrophenoxyacetyl, acrylyl(Acr), chloroacetyl, acetyl(Ac) and γ-chlorobutyryl; (2) aromatic urethan-type protecting groups, e.g., benzyloxycarbonyl(Z), fluorenylmethyloxycarbonyl(Fmoc) and substituted benzyloxycarbonyl, such as p-chlorobenzyloxycarbonyl(ClZ), p-nitrobenzyloxycarbonyl, p-bromobenzyloxycarbonyl and p-methoxybenzyloxycarbonyl; (3) aliphatic urethane protecting groups, such as tertbutyloxycarbonyl(Boc), diisopropylmethoxycarbonyl, isopropyloxycarbonyl, ethoxycarbonyl and allyloxycarbonyl; (4) cycloalkyl urethane-type protecting groups, such as cyclopentyloxycarbonyl, adamantyloxycarbonyl and cyclohexyloxycarbonyl; (5) thiourethane-type protecting groups, such as phenylthiocarbonyl; (6) alkyl-type protecting groups, such as allyl(Aly), triphenylmethyl (trityl) and benzyl(Bzl); (7) trialkylsilane groups, such as trimethylsilane. The preferred $\alpha$-amino protecting group is Boc.

$X^2$ is hydrogen or a protecting group for the phenolic hydroxyl group of Tyr selected from the group consisting of tetrahydropyranyl, tert-butyl, trityl, benzyl, Z, 2-bromobenzyloxycarbonyl(2BrZ) and 2,6-dichlorobenzyl (DCB). 2BrZ is preferred.

$X^3$ is a protecting group for Cys preferably selected from the class consisting of p-methoxybenzyl(Mob), p-methylbenzyl, acetamidomethy, trityl and Bzl. The most preferred protecting group is p-methoxybenzyl. $X^3$ can also be hydrogen, meaning that there is no protecting group on the sulfur.

$X^4$ is a protecting group for an amino side chain group, primary or secondary amino, such as that of Lys. Illustrative of suitable side chain amino protecting groups are Z, 2-chlorobenzyloxycarbonyl(2-Cl-Z), Tos, t-amyloxycarbonyl and Boc. The selection of a side chain amino protecting group is not critical except that it must be one which is not removed during deprotection of the a-amino groups during the synthesis. Hence, the $\alpha$-amino protecting group and the side chain amino protecting group cannot be the same.

$X^5$ is hydrogen or a protecting group for the indole nitrogen of Trp, such as Bz, Ac or For. In many syntheses there is no need to protect Trp.

$X^6$ is hydrogen or a protecting group for the hydroxyl side chain of Thr or Ser, e.g. Ac, Bz, trityl, DCB or benzyl ether(Bzl) and is preferably Bzl.

$X^7$ is selected from the class consisting of OH, $OCH_3$ and esters, including a benzyl ester or a hydroxymethyl ester anchoring bond used in solid-phase synthesis for linking to a solid resin support, represented by the formulae:

—O—$CH_2$-polystyrene resin support and

O—$CH_2$-benzyl-polystyrene resin support

Such a polystyrene polymer is preferably a copolymer of styrene with about 0.5 to 2% divinyl benzene as a cross-linking agent, which causes the polystyrene polymer to be completely insoluble in certain organic solvents.

The criterion for selecting certain side chain protecting groups for $X^2$-$X^6$ is that the protecting group should be stable to the reagent under the reaction conditions selected for removing the $\alpha$-amino protecting group (preferably Boc) at each step of the synthesis. These protecting groups generally should not be split off under coupling conditions but should be removable upon completion of the synthesis of the desired amino acid sequence under reaction conditions that will not alter the peptide chain. A protecting group initially employed for a certain 8-position residue may be removed prior to cleavage from the resin to carry out a reaction at that position, as explained hereinafter. Similarly, the 9-position residue in the form of the aminomethylPhe (Amp) may be introduced in its final desired form, or it may be deprotected and alkylated, if desired, while part of the resin-peptide.

Thus, there is broadly provided a method for making a SRIF analog peptide having the formula:

(cyclo 3-14)H-$Xaa_2$-Cys-Lys-Phe-Phe-D-$Xaa_8$-$Xaa_9$-Thr-Phe-Thr-$Xaa_{13}$-Cys-OH wherein $Xaa_2$, D-$Xaa_8$, $Xaa_9$ and $Xaa_{13}$ are as set forth hereinbefore, which method comprises (a) forming an intermediate peptide having the formula:
$X^1$-$Xaa_2(X^2)$-Cys($X^3$)-Lys($X^4$)-Phe-Phe-D-$Xaa_8(X^5)$-$Xaa_9$ ($X^3$)-Thr($X^6$)-Phe-Thr($X^6$)-$Xaa_{13}(X^3)$-Cys wherein $X^1$ is hydrogen or an $\alpha$-amino protecting group; $X^5$ is hydrogen or a protecting group for an indole nitrogen; $X^6$ is a protecting group for a hydroxyl group of Thr or Ser; $X^2$ is hydrogen or a protecting group for a phenolic hydroxyl group of Tyr; $X^3$ is either hydrogen or a protecting group for a sulfhydryl side chain; $X^4$ is a protecting group for an amino side chain, $X^7$ is —O—$CH_2$-[resin support], or a protecting group or OH, (b) splitting off any remaining groups $X^1$ to $X^6$ and/or cleaving from any resin support included in $X^7$; (c) oxidizing to create a disulfide bond between the Cys side chains; and (d) converting to a nontoxic salt, if desired.

Purification of the peptide is effected by ion exchange chromatography on a CMC column, followed by partition chromatography using the elution system: n-butanol;0.1N acetic acid (1:1 volume ratio) on a column packed with Sephadex G-25, or by using HPLC, as known in the art and specifically set forth in J. Rivier, et al. *J. Chromatography*, 288, 303–328 (1984).

The SRIF analogs of the invention are effective at levels of less than 100 micrograms per kilogram of body weight. For prolonged suppression of cancerous tumors having SSTR1 receptors, it may be necessary to use dosage levels in the range of from about 0.1 to about 2.5 milligrams per kilogram of body weight. These analogs are particularly soluble at physiological pHs and thus can be prepared as relatively concentrated solutions for administration.

The following Examples illustrate the syntheses of a number of SRIF analog peptides embodying various features of the invention, together with the syntheses of a protected amino acids for use in such peptide syntheses. All of these peptides include at least one D-isomer amino acid residue, and although the preferred SRIF analogs do not include 14 amino acid residues, to permit ready comparison with the native SRIF sequence, the peptide analogs are described by making reference to the comparable positions in the native SRIF sequence having positions 1 through 14, with the Cys residues in positions 3 and 14 being joined by the cyclizing disulfide bond.

EXAMPLE 1

The synthesis of L-$N^\alpha$-Boc-$N^4$-Cbz-(4-isopropylaminomethyl)phenylalanine, which is referred to by the shorthand nomenclature as Boc-IAmp(Z), is carried out as follows:

L-$N^\alpha$-Boc-(4-aminomethyl)phenylalanine (Boc-Amp) (15.3 g, 52 mmol) is dissolved in acetone (200 mL), and molecular sieves (6.0 g, 4 Å) are added to the solution in a 500 mL Parr hydrogenation vessel. The mixture is purged with $N_2$ for 10 minutes; then Pd/C 10% (600 mg) is added. A reductive alkylation reaction occurs and is monitored by HPLC; it is carried out for about 26 hours. After filtration to remove the catalyst and molecular sieves and evaporation of the solvent, the desired intermediate L-$N^\alpha$-Boc-(4-isopropylaminomethyl)phenylalanine is obtained as a viscous liquid.

The product is then Cbz-protected using benzyl chloroformate (Z-Cl, 8.6 mL, 60 mmol) in a mixture of THF/$H_2O$ (1:1,200 mL) at pH=9.5. A good yield of L-$N^\alpha$-Boc-$N^4$-Cbz-(4-isopropylaminomethyl)phenylalanine is obtained as a foam: 17.5 g (37 mmol, 71.4%); m.p. 39°–42° C.; $[\alpha]_D$= +5.2° (c=1, MeOH, t=20° C.).

EXAMPLE 2

The somatostatin agonist des-$AA^{1,2,5}$[D-$Trp^8$, $IAmp^9$]-SRIF having the structure:

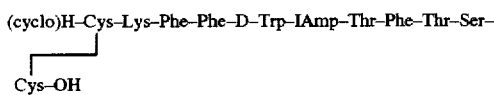

is synthesized by the following solid phase methodology in a stepwise manner on a chloromethylated resin. The resin is composed of fine beads (20–70 microns in diameter) of a synthetic resin prepared by copolymerization of styrene with one to two percent divinylbenzene. The benzene rings in the resin are chloromethylated in a Friedel-Crafts reaction with chloromethyl methyl ether and stannic chloride. The chlorine thus introduced creates a reactive benzyl chloride type of linker. The Friedel-Crafts reaction is continued until the resin contains 0.5 to 2 millimoles of chlorine per gram of resin.

The tert-butyloxycarbonyl-S-paramethoxybenzyl derivative of Cys, i.e. Boc-Cys(Mob), is linked to the resin by a known method, such as: (1) reflux in ethanol in presence of triethylamine, (2) cesium salt of the Boc-protected amino acid is kept at 50° C. in dimethylformamide (DMF) overnight or (3) Boc-protected amino acid is kept at 80° C. in N-methypyrrolidone (NMP) for 24 hours in the KF. One milliequivalent of the protected Cys per milliequivalent of Cl on the resin is used. Deprotection, neutralization and addition of each amino acid is performed in accordance with the following schedule:

| STEP | REAGENTS AND OPERATIONS | MIX TIMES (MIN.) |
|---|---|---|
| 1 | $CH_2Cl_2$ wash-80 ml. (2 times) | 3 |
| 2 | Methanol (MeOH) wash-30 ml. (2 times) | 3 |
| 3 | $CH_2Cl_2$ wash-80 ml. (3 times) | 3 |
| 4 | 50% TFA plus 5% meta-cresol in $CH_2Cl_2$ -70 ml. (2 times) | 20 |
| 5 | Isopropyl alcohol + 1% meta-cresol wash-80 ml. (2 times) | 3 |
| 6 | TEA 12.5% in $CH_2Cl_2$-70 ml. | 5 |
| 7 | MeOH wash-40 ml. (2 times) | 2 |
| 8 | TEA 12.5% in $CH_2Cl_2$-70 ml. (2 times) | 2 |
| 9 | $CH_2Cl_2$ wash-80 ml. (3 times) | 3 |
| 10 | Boc-amino acid (5 mmoles) in 30 ml. of $CH_2Cl_2$ (DCM) or dimethylformamide (DMF): DCM or NMP:DCM, depending upon the solubility of the particular protected amino acid, plus DIC or DCC (5 mmoles) in $CH_2Cl_2$ | 30–300 |
| 11 | MeOH wash-40 ml. (2 times) | 3 |
| 12 | Triethylamine (TEA) 12.5% in $CH_2Cl_2$-70 ml. | 3 |
| 13 | MeOH wash-30 ml. (2 times) | 3 |
| 14 | DCM wash-80 ml. (2 times) | 3 |

The Boc derivative of each amino acid is used. After α-amino deprotection of the first residue, i.e., Boc-Cys (Mob), according to the above schedule, the $N^\alpha$Boc derivative of Ser is added along with the coupling agent, dicyclohexylcarbodiimide (DCC), the side chain of Ser being protected with benzyl ether (Bzl). The $N^\alpha$Boc derivative of Thr(Bzl) is next added along with DCC. After coupling $N^\alpha$Boc-Phe and then $N^\alpha$Boc-Thr(Bzl), $N^\alpha$Boc-4-isopropylaminomethyl Phe(Z) is similarly coupled.

$N^\alpha$Boc-Lys(2-ClZ) is next added, and then the remaining protected Cys is coupled to extend the peptide chain to the N-terminus. This creates the intermediate: Boc-Cys(Mob)-Lys(2-ClZ)-Phe-Phe-D-Trp-IAmp(Z)-Thr(Bzl)-Phe-Thr (Bzl)-Ser(Bzl)-Cys(Mob)-O—$CH_2$-resin support.

Cleavage of the peptide from the resin and deprotection of the side chain protecting groups are performed in hydrofluoric acid(HF) (25 ml) in the presence of 2 ml of anisole and 2 ml of dimethylsulfide for 1.5 hours at 0° C. after 20 minutes at ambient temperature. After elimination of hydrofluoric acid under high vacuum, the resin-peptide is washed with anhydrous diethyl ether.

The resin is immediately extracted with 75% acetic acid (200 ml). The extract is filtered into a 500 milliliter round-bottom flask and is then oxidized to create the disulfide cyclic linkage by stirring vigorously while rapidly adding a 10 weight percent solution of iodine in methanol until the resultant solution remains orange-colored. It is then stirred for 10–20 additional minutes and quenched with 10% ascorbic acid in water until the yellow color is gone. Concentration under vacuum is carried out to reduce the volume to about 50 milliliters, followed by dilution to about 300 milliliters with water. The solution is then applied to a 4 centimeter by 7 centimeter pad of $C_{18}$ silica in a coarse-fritted funnel that was previously equilibrated with 5% $CH_3CN$ in 0.1% trifluoroacetic acid (TFA) in water. Following vacuum filtration, the eluate is diluted to 500 milliliters and reapplied to the pad. The eluate is collected and diluted to about 800 ml, and filtration is repeated. Thereafter, the pad is washed with about 300 milliliters of 5% acetonitrile in 0.1% TFA, and the peptide is eluted using about 250 milliliters of 60% $CH_3CN$ in water. The resultant solution is diluted to about 500 milliliters with distilled water, frozen and lyophilized.

The lyophilized material is then purified by subjection to analytical HPLC on a $C_{18}$ column. Peaks are located which are then individually purified using buffer systems as disclosed in Hoeger et al., *Biochromatography*, 2, 134–142 (1987). Final analytical HPLC is carried out using a gradient of Buffer B from 30% to 60% over 30 minutes with Buffer A being 0.1% aqueous TFA and Buffer B being 60% $CH_3CN$ in Buffer A. The desired cyclic peptide

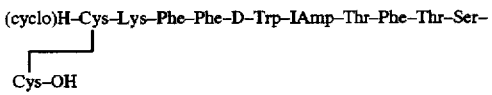

is obtained which appears to be greater than 97% pure on capillary zone electrophoresis.

MS analysis shows the expected mass of 1485.7 Da. The specific optical rotation measures $[\alpha]_D^{22} = -10.3° \pm 1°$ (c=0.5 in 50% acetic acid)

The peptide is hereinafter referred to as Peptide No. 2.

EXAMPLE 2A

The synthesis described in Example 2 is repeated with one change. $N^\alpha$Boc-$N^4$-CBZ-(4-aminomethyl) phenylalanine, i.e. Boc-Amp, is used to provide the 9-position residue. Further elongation of the chain then proceeds as in Example 2, and cleavage, deprotection, cyclization and purification are carried out as in Example 2

The purified cyclic peptide has the formula:

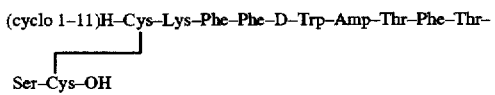

and is referred to as Peptide No. 2A.

EXAMPLE 2B

The initial synthesis described in Example 2A is repeated with one change; $N^\alpha$Boc-$N^4$-Fmoc-(4-aminomethyl)

phenylalanine, i.e. Boc-Amp(Fmoc), is used to provide the 9-position residue. Further elongation of the chain then proceeds as in Example 2A, until the final coupling with Boc-Cys(Mob) is effected.

With the N$^\alpha$Boc group still in place at the N-terminus, the side chain of Amp is alkylated. The Fmoc protecting group is selectively removed by treatment with 20 percent piperidine in NMP or DMF(10 ml.) for about 15 minutes; the intermediate is preferably washed with NMP and then treated with more piperidine/NMP for another 15 minutes. After preferably washing the peptidoresin with NMP, the newly freed aminomethyl groups are treated with (MeO-phenyl)$_2$-CHCl, which is referred to as Dod-Cl, in NMP plus diisopropyl ethylamine (DIEA) for 1-2 hours. After washing, the peptidoresin (about 1-2 g) is treated for 20 minutes with 6 mls of 36% formaldehyde and 10 mls of 1% acetic acid in NMP, adding 0.35 gram of cyanoborohydride (NaBH$_3$CN); at the end of 20 minutes, this treatment is repeated one more time. This reaction adds a single methyl group to the aminomethylPhe side chain. Details of the reaction are found in Kaljuste and Unden, *Int. J. Peptide Protein Res.*, 42, 118–124 (1993). The usual washing is carried out, and then the Dod-Cl protecting group and the Boc group at the N-terminus are removed by treatment with 60% TFA in DCM for 20 minutes. Cleavage, deprotection, cyclization and purification are then carried out as in Example 2. The purified cyclic peptide has the formula:

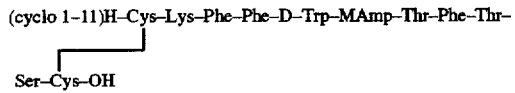

and is referred to as Peptide No. 2B.

EXAMPLE 2C

The synthesis described in Example 2B is repeated with one change. Instead of reacting the protected aminomethyl moiety with 36% formaldehyde, the reaction is carried out for 20 minutes with 15 mls of a solution of 40% acetaldehyde in 1% acetic acid in NMP, plus 0.35 gm. of cyanoborohydride and repeated once. This results in the (MeO-phenyl)$_2$-CHCl(4-ethyl aminomethyl) phenylalanine as the 9-position residue. Removal of the Boc and Dod-Cl groups, cleavage, deprotection, cyclization and purification are carried out as in Example 2B. The purified cyclic peptide has the formula:

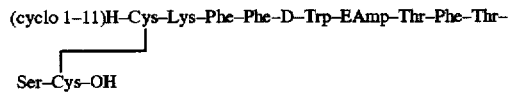

and is referred to as Peptide No. 2C.

EXAMPLE 2D

The synthesis described in Example 2B is repeated with one change. Instead of reacting the protected aminomethyl moiety with 36% formaldehyde, the reaction is carried out for 20 minutes with 15 mls of a solution of 40% isobutyraldehyde in 1% acetic acid in NMP, plus 0.35 gm. of cyanoborohydride and repeated once. This results in the (MeO-phenyl)$_2$-CHCl(4-isobutyl aminomethyl) phenylalanine as the 9-position residue. Removal of the Boc and Dod-Cl groups, cleavage, deprotection, cyclization and purification are carried out as in Example 2B. The purified cyclic peptide has the formula:

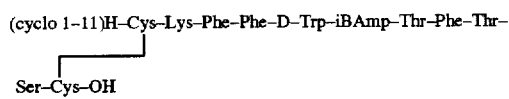

and is referred to as Peptide No. 2D.

Peptide Nos. 2A, 2B, 2C and 2D bind selectively to SSTR1.

EXAMPLE 3

The synthesis described in Example 2 is repeated with one change. Instead of coupling Boc-D-Trp as what is referred to as the 8-position residue, N$^\alpha$Boc-D-2Nal is used. Further elongation of the chain then proceeds as in Example 2.

Cleavage, deprotection, cyclization and purification are carried out as in Example 2. Amino acid analysis shows the expected ratio for the different amino acids. The purified cyclic peptide has the formula:

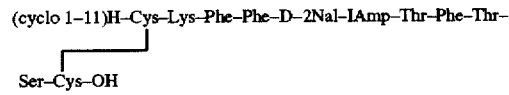

and is referred to as Peptide No. 3A.

The synthesis is repeated, substituting N$^\alpha$Boc-D-1Nal for N$^\alpha$Boc-D-2Nal to obtain the following purified cyclic peptide, which is referred to as Peptide No. 3B:

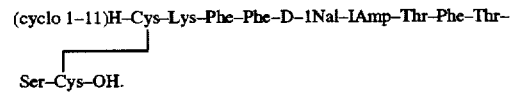

Both Peptides Nos. 3A and 3B bind selectively to human SSTR1.

EXAMPLE 4

The synthesis described in Example 2 is repeated with one change. Instead of coupling Boc-Ser(Bzl) as what is referred to as the 13-position residue, N$^\alpha$Boc-D-Ser(Bzl) is used. Elongation of the chain is then carried out as in Example 2.

Cleavage, deprotection, cyclization and purification are carried out as in Example 2. HPLC and CZE show the peptide to have a purity of greater than 97%. The specific optical rotation measures
$[\alpha]_D^{22}=+20.0°\pm1°$ (c=0.5 in 50% acetic acid)
Amino acid analysis shows the expected ratio for the different amino acids. MS analysis shows the expected mass of 1485.7 Da. The purified cyclic peptide has the formula:

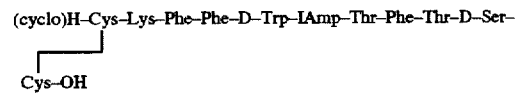

and is referred to as Peptide No. 4.

EXAMPLE 5

The synthesis described in Example 2 is again repeated with one change. Elongation of the chain by one residue is carried out by coupling N$^\alpha$Boc-Tyr(2BrZ) at the N-terminus.

Cleavage, deprotection, cyclization and purification are carried out as in Example 2. The specific optical rotation measures $[\alpha]_D^{22} = -9.6° \pm 1°$ (c=0.5 in 50% acetic acid)

Amino acid analysis shows the expected ratio for the different amino acids. MS analysis shows the expected mass of 1648.7 Da. The purified cyclic peptide has the formula:

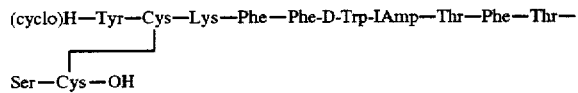

and is referred to as Peptide No. 5.

EXAMPLE 6

The synthesis described in Example 2 is repeated with one change. Instead of coupling Boc-D-Trp as what is referred to as the 8-position residue, $N^\alpha$Boc-D-3-Pal is used. Elongation of the chain is then carried out as in Example 2.

Cleavage, deprotection, cyclization and purification are carried out as in Example 2. The purified cyclic peptide has the formula:

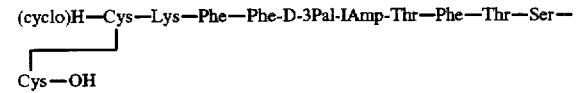

and is referred to as Peptide No. 6A.

The above synthesis is then repeated 22 times, each time substituting a different amino acid at position 8, as follows:

$N^\alpha$Boc-D-5ClTrp;

$N^\alpha$Boc-D-6FTrp;

$N^\alpha$Boc-D-5NO$_2$Trp;

$N^\alpha$Boc-D-6BrTrp;

$N^\alpha$Boc-D-N$^{in}$ForTrp;

$N^\alpha$Boc-3-(9-fluorenyl)-D,L-Ala;

$N^\alpha$Boc-3-(1-adamantyl)-D,L-Ala;

$N^\alpha$Boc-3-(4-biphenylyl)-D,L-Ala;

$N^\alpha$Boc-3-(2-anthryl)-D,L-Ala;

$N^\alpha$Boc-3-(2,4,6-triethylphenyl)-D,L-Ala;

$N^\alpha$Boc-3-(9-anthryl)-D,L-Ala;

$N^\alpha$Boc-3-(2-fluorenyl)-D,L-Ala;

$N^\alpha$Boc-3-(1-anthryl)-D,L-Ala;

$N^\alpha$Boc-D,L-Me5-Phe;

$N^\alpha$Boc-D,L-TMP;

$N^\alpha$Boc-D,L-BIA;

$N^\alpha$Boc-D,L-TBA;

$N^\alpha$Boc-3-(3-phenanthryl)-D,L-Ala;

$N^\alpha$Boc-3-(2,4,6-trimethylcyclohexyl)-D,L-Ala;

$N^\alpha$Boc-3-(perhydro-4-biphenylyl)-D,L-Ala;

$N^\alpha$Boc-3-(1-perhydronaphthyl)-D,L-Ala; and $N^\alpha$Boc-3-(2,2-diphenylmethyl)-D,L-Ala The resultant SRIF analogs are referred to as peptides 6B through 6W.

Peptides 6A–6W bind selectively to SSTR1.

EXAMPLE 7

A betide somatostatin agonist des-AA$^{1,2,5}$[Agl (indolecarboxyl)$^8$, IAmp$^9$]-SRIF having the structure:

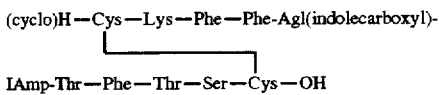

is synthesized by the following solid phase methodology described in Example 2 using a chloromethylated resin.

The Boc derivative of each amino acid is used. After deprotection of the first residue, i.e., Boc-Cys (Mob), according to the schedule set forth in Example 2, the $N^\alpha$Boc derivative of Ser is added along with the coupling agent, dicyclohexylcarbodiimide(DCC), the side chain of Ser being protected with O-benzyl ether (Bzl). The $N^\alpha$Boc derivative of Thr(Bzl) is next added along with DCC. After coupling $N^\alpha$Boc-Phe and then $N^\alpha$Boc-Thr(Bzl), $N^\alpha$Boc-4-isopropylamino Phe(Z) is similarly coupled.

Then Boc-D/L-Agl(Fmoc) is coupled in the 8-position, followed by the coupling of 2 residues of $N^\alpha$Boc-Phe. Benzyloxycarbonyl-2Cl, i.e. 2ClZ, is used as the protecting group for the Lys side chain in the 4-position of SRIF. The final protected Cys is coupled to extend the peptide chain to the N-terminus. With the $N^\alpha$Boc group still in place at the N-terminus, the side chain of Agl is modified. The Fmoc protecting group is selectively removed by treatment with 20 percent piperidine in NMP or DMF(10 mL) for about 15 minutes; the intermediate is preferably washed with DMF and then treated with more piperidine/DMF for another 15 minutes. After preferably washing the peptidoresin with DMF, the newly freed amino groups are reacted with indole-3-carboxyl acid using a suitable coupling agent such as TBTU or HBTU or BOP for about 10 hours.

Cleavage of the betide from the resin and deprotection of the side chain protecting groups of the betide are performed in hydrofluoric acid(HF) (25 ml) in the presence of 2 ml of anisole and 2 ml of dimethylsulfide for 1.5 hours at 0° C. after 20 minutes at ambient temperature. After elimination of HF under high vacuum, the resin-betide is washed with anhydrous diethyl ether.

The resin is then extracted, cyclized and lyophilized as generally described in Example 2. The lyophilized material is then purified by subjection to analytical HPLC on a $C_{18}$ column. Peaks are located which are then individually purified using similar buffer systems. Final analytical HPLC is carried out using a gradient of Buffer B from 30% to 60% over 30 minutes, with Buffer A being 0.1% aqueous TFA and Buffer B being 60% CH$_3$CN in Buffer A. The desired cyclic betides

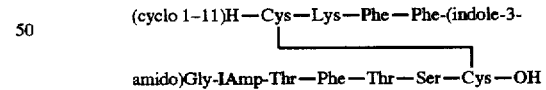

are obtained in the form of two separate diastereomers which appear to be greater than 97% pure on capillary zone electrophoresis. Both the cyclic betides bind to SSTR1.

EXAMPLE 8

A synthesis generally as described in Example 2 is carried out to synthesize [IAmp$^5$]-ODT8 which has the formula:

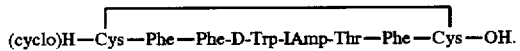

Cleavage, deprotection, cyclization and purification are carried out as in Example 2. HPLC and CZE show the peptide to have a purity of greater than 97%. The specific optical rotation measures $[\alpha]_D^{22} = -35° \pm 1°$ (c=1 in 50% acetic acid)

Amino acid analysis shows the expected ratio for the different amino acids.

EXAMPLE 9

The synthesis described in Example 2 is repeated with one change. Before coupling Boc-Lys(2ClZ) in the chain, BocAsn(Xan) is coupled as the 5-position residue. Further elongation of the chain then proceeds as in Example 2.

Cleavage, deprotection, cyclization and purification are carried out as in Example 2. Amino acid analysis shows the expected ratio for the different amino acids. The purified cyclic peptide has the formula:

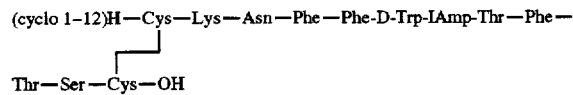

is referred to as Peptide No. 9.

The synthesis is then repeated, adding $N^\alpha$Boc-Gly and $N^\alpha$Boc-Ala at the N-terminus to obtain the following purified cyclic peptide, which is referred to as Peptide No. 9A:

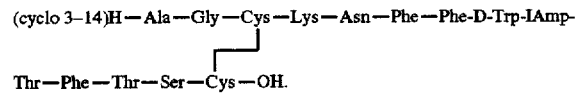

It is [D-Trp$^8$, IAmp$^9$]SRIF.

Both Peptides Nos. 9 and 9A bind selectively to human SSTR1.

In vitro Bioassay: The effects of the various somatostatin analogs are tested in vitro for their ability to bind to isolated cloned receptors expressed on COS and CHO cells.

The molecular cloning of the genes encoding multiple somatostatin receptor subtypes permits the individual expression of these receptors in mammalian cells and the characterization of their respective pharmacological profiles. Five such receptor subtypes, termed SSTR1 through SSTR5, have been cloned and are reported and described in Raynor et al., *Molecular Pharmacology*, 43, 838–844 (1993) and in Raynor et al., *Molecular Pharmacology*, 44, 385–392 (1993), the disclosures of which are incorporated herein by reference. These references describe binding assays that can be used to determine whether particular SRIF analogs bind selectively to one or more of the 5 receptor types and also whether they bind to such receptor types with high or low affinity. Because these receptor types have now been characterized with regard to their pharmacological profiles, knowledge of the results of such binding studies along with knowledge of the unique patterns of distribution of these receptors in the body indicate that each receptor subtype may mediate distinct but overlapping physiological effects of SRIF; therefore, compounds which bind selectively to receptors SSTR1, for example, can be used to modulate a particular physiological function of SRIF without potentially having an undesired effect resulting from another physiological function of SRIF which is mediated by other SRIF receptors.

To test the selectivity of Peptide No. 2 to bind to the SRIF receptors, the ability of this peptide to inhibit the binding of [$^{125}$I-Tyr$^{11}$]SRIF to the five cloned SRIF receptors was first tested. Previous studies had shown that [$^{125}$I-Tyr$^{11}$]SRIF binds to all five cloned SRIF receptors with similar affinities. At concentrations of 1 μM, Peptide No. 2 had minimal effects on the binding of [$^{125}$I-Tyr$^{11}$]SRIF to mouse SSTR2 and SSTR3, to human SSTR4 and to rat and human SSTR5. In contrast, it potentially displaced the binding of [$^{125}$I-Tyr$^{11}$]SRIF to human SSTR1 with an IC$_{50}$ value of 1.8±0.7 nM. Similarly, Peptide No. 4 containing the D-Ser$^{13}$ modification selectively bound to SSTR1, and Peptide No. 5, the tyrosine analog, also selectively interacts with SSTR1.

To investigate whether an iodinated analog of Peptide No. 5 may serve as a selective SSTR1 radioligand, the peptide was iodinated and tested for binding to the five cloned SRIF receptors. No specific binding of Peptide No. 5 to SSTR2–5 was detectable. In contrast, Peptide No. 5 effectively bound to SSTR1 to about the same extent as [$^{125}$I-Tyr$^{11}$]SRIF.

The binding of Peptide No. 5 to SSTR1 reached equilibrium by 30 minutes. The binding was saturable with a Kd of 0.5±0.1 nM and a Bmax of 226±56 fmol/mg protein. SRIF, [D-Trp$^8$]SRIF and SRIF-28 all potently inhibited binding of Peptide No. 5 to SSTR1 with IC$_{50}$ values of 0.8±0.4, 0.2±0.1 nM and 0.7±0.2 nM, respectively. The SRIF analog Peptide No. 4 also potently binds to SSTR1 exhibiting an IC$_{50}$ value of 5.3±0.8 nM, based upon its ability to inhibit the binding of iodinated Peptide No. 5.

Previous studies with SSTR1 expressed in COS-07 cells have shown that the binding of [$^{125}$I-Tyr$^{11}$]SRIF to SSTR1 is not significantly effected by FTPgS nor pertussis toxin pretreatment, suggesting that this receptor may not be effectively coupled to G proteins. Similarly, GTPgS and pertussis toxin treatment did not diminish the binding of [$^{125}$I-Tyr$^{11}$]SRIF binding to the cloned SSTR1. However, GTPgS significantly reduced the binding of Peptide No. 5 to SSTR1, in a concentration-dependent manner. Overnight pertussis toxin treatment diminished the effect of GTPgS, i.e. GTPgS was no longer able to significantly affect binding to pertussis toxin-pretreated SSTR1. These findings suggest that SSTR1 can couple to pertussis toxin-sensitive G proteins and that differences in association of the receptor with G proteins occur following SRIF binding to the receptor versus the binding of one of the peptides of the present invention.

Because the binding of Peptide No. 5 was GTP regulated, the ability of the peptide to modulate cAMP accumulation in COS-7 cells expressing SSTR1 was tested. Neither 1 μM of Peptide No. 2, nor SRIF itself, inhibits forskolin-stimulated cAMP formation in COS-7 cells expressing SSTR1. Therefore, while Peptide No. 2 can induce an apparent association of SSTR1 with pertussis toxin G proteins, it does not appear to regulate adenylyl cyclase activity in COS-7 cells.

Screening assays as are well known in the art which employ the receptor polypeptide SSTR1 directly from the recombinant host can be used to identify agents useful in mimicking the desirable aspects of somatostatin while eliminating the undesirable aspects of the hormone which may arise from activation of other receptors.

The potencies of certain SRIF analogs, including the prior art compound ODT8, (cyclo 1-8)H-Cys-Phe-Phe-D-Trp-Lys-Thr-Phe-Cys-OH, to inhibit radioligand binding of [$^{125}$I-Tyr$^{11}$]SRIF to the various cloned mouse SRIF receptors, relative to SRIF and SRIF-28, are shown in the following table wherein the IC$_{50}$ values are given in nanomolar concentration. Certain of the measurements are in progress.

TABLE

| Compound | IC₅₀ (nM) | | | | |
|---|---|---|---|---|---|
| | mSSTR1 | mSSTR2 | mSSTR3 | mSSTR4 | mSSTR5 |
| SRIF | 0.10 | 0.28 | 0.08 | 1.2 | 0.86 |
| SRIF-28 | 0.07 | 0.43 | 0.07 | 0.29 | 0.23 |
| ODT8 | 1 | 35 | 4 | 0.9 | 2 |
| Peptide No. 2 | 1 | 1100 | 1000 | 700 | 650 |
| Peptide No. 4 | 1.25 | >1000 | 178 | >1000 | 472 |
| Peptide No. 5 | 0.8 | >>100 | >>100 | >>100 | >>100 |
| [IAmp⁹] ODT8 | 160 | >1000 | 500 | >1000 | >1000 |
| Peptide No. 9 | 54 | >1000 | >1000 | >1000 | 1100 |

The peptides of the invention not only provide more selective ligands for binding SSTR1 but the use of a labelled Peptide No. 5, e.g. with $^{125}$I, facilitates drug screening for even more effective agonists. Competitive binding assays with candidate compounds would first be carried in this manner with SSTR1 to search for high binding affinity; then by screening the multiple SRIF receptors, it could be confirmed whether there was selective binding to only this receptor as is desired.

These SRIF analogs or nontoxic salts thereof, combined with a pharmaceutically or veterinarily acceptable carrier to form a pharmaceutical composition, may be administered to animals, including humans and other mammals, either intravenously, subcutaneously, intramuscularly, percutaneously, e.g. intranasally, intracerebrospinally or orally. The peptides should be at least about 90% pure and preferably should have a purity of at least about 98%; however, lower purities are effective and may well be used with mammals other than humans. This purity means that the intended peptide constitutes the stated weight % of all like peptides and peptide fragments present. Administration to humans should be under the direction of a physician to combat specific tumors and cancers or to mediate other conditions where the SSTR1 receptors exert a control function, such as coupling to a tyrosine phosphatase so that stimulation of this enzyme can be carried out to mediate the anti-proliferative effects of SRIF. The required dosage will vary with the particular condition being treated, with the severity of the condition and with the duration of desired treatment.

Such peptides are often administered in the form of pharmaceutically or veterinarily acceptable nontoxic salts, such as acid addition salts or metal complexes, e.g., with zinc, iron, calcium, barium, magnesium, aluminum or the like. Illustrative of such nontoxic salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

It may also be desirable to deliver these SRIF analogs over prolonged periods of time, for example, for periods of one week to one year from a single administration, and slow release, depot or implant dosage forms may be utilized as well known in this art. For example, a dosage form may contain a pharmaceutically acceptable non-toxic salt of the compound which has a low degree of solubility in body fluids, for example, an acid addition salt with a polybasic acid; a salt with a polyvalent metal cation; or combination of the two salts. A relatively insoluble salt may also be formulated in a gel, for example, an aluminum stearate gel. A suitable, slow-release depot formulation for injection may also contain an SRIF analog or a salt thereof dispersed or encapsulated in a slow degrading, non-toxic or non-antigenic polymer such as a polylactic acid/polyglycolic acid polymer, for example, as described in U.S. Pat. No. 3,773,919.

Therapeutically effective amounts of the peptides should be administered under the guidance of a physician, and pharmaceutical compositions will usually contain the peptide in conjunction with a conventional, pharmaceutically or veterinarily-acceptable carrier. A therapeutically effective amount is considered to be a predetermined amount calculated to achieve the desired effect. The required dosage will vary with the particular treatment and with the duration of desired treatment; however, it is anticipated that dosages between about 10 micrograms and about 1 milligram per kilogram of body weight per day will be used for therapeutic treatment. It may be particularly advantageous to administer such compounds in depot or long-lasting form as earlier described. A therapeutically effective amount is typically an amount of an SRIF analog that, when administered peripherally, e.g. intravenously, in a physiologically acceptable composition, is sufficient to achieve a plasma concentration thereof from about 0.1 µg/ml to about 100 µg/ml, preferably from about 1 µg/ml to about 50 µg/ml, more preferably at least about 2 µg/ml and usually 5 to 10 µg/ml.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. Although the claims variously define the invention in terms of a peptide sequence, it should be understood that such is intended to include nontoxic salts thereof which are well known to be the full equivalent thereof and which are most frequently administered. Instead of the simple free acid at the C-terminus, a lower alkyl ester may be incorporated as well known in the peptide art. Cyclic peptides having an amino acid residue sequence substantially identical to the sequence of the SRIF analogs specifically shown herein, in which one or more residues have been conservatively substituted with a functionally similar amino acid residue, are considered to be equivalents so long as they selectively bind to SSTR1.

As previously indicated, these specified modifications can be incorporated in previously disclosed SRIF analogs to create SSTR1-selectivity. Incorporation of a residue in the 5-position is optional, but not preferred, because it generally detracts from binding affinity although selectivity remains. Likewise inclusion of residues in the 1- and 2-position is optional, but except for Tyr or D-Tyr, is not considered worthwhile. Broadly it is considered that cyclic somatostatin analog peptides can be created having specific affinity for the SRIF receptor SSTR1 by modifying the amino acid sequence of existing SRIF analogs known in the art to have SRIF biological activity. The modified peptide should have an amino acid sequence at least 8 residues in length, contain a Cys-Cys disulfide bond with a sequence of at least 6 residues located between said Cys residues as a ring, and contain D-Trp or its equivalent centrally of such sequence of at least 6-residue sequence, preferably spaced by 2 or 3 residues from the Cys residue at or near the N-terminus, which analog peptide is characterized by the presence of (C)Amp joined immediately C-terminally to said D-Trp, with C being H or lower alkyl. The disclosed cyclic SRIF analogs may also be modified by N-methylation of the α-amino group on one (or two) of the residues, preferably those in the 7–10 positions of SRIF, e.g. des-AA$^{1,2,5}$ [N$^\alpha$CH$_3$D-Trp$^8$, IAmp$^9$]-SRIF. The resulting SRIF analogs retain their specificity for SSTR1, and in some instances have greater binding affinity. Such peptides and salts thereof are considered as being within the scope of the claimed invention.

The disclosures of all patents and publications set forth hereinbefore are expressly incorporated herein by reference. As used herein, all temperatures are °C. and all ratios are by volume. Percentages of liquid materials are also by volume.

Various features of the invention are emphasized in the claims which follow.

What is claimed is:

1. A cyclic somatostatin (SRIF) analog peptide having specific affinity for the SRIF receptor SSTR1, which peptide has the amino acid sequence (cyclo 3-14)Xaa$_1$-Xaa$_2$-Cys-Lys-Xaa$_5$-Phe-Phe-D-Xaa$_8$-Xaa$_9$-Thr-Phe-Thr-Xaa$_{13}$-Cys wherein Xaa$_1$ is des-Xaa or Ala; Xaa$_2$ is Tyr, D-Tyr or des-Xaa or Gly; Xaa$_5$ is des-Xaa or Asn; D-Xaa$_8$ is an aromatic D-amino acid; Xaa$_9$ is (C)aminomethyl Phe with C being H or lower alkyl; and Xaa$_{13}$ is Ser or D-Ser.

2. A cyclic somatostatin (SRIF) analog peptide having specific affinity for the SRIF receptor SSTR1, which peptide has the amino acid sequence (cyclo 3-14)Xaa$_1$-Xaa$_2$-Cys-Lys-Xaa$_5$-Phe-Phe-D-Xaa$_8$-Xaa$_9$-Thr-Phe-Thr-Xaa$_{13}$-Cys wherein Xaa$_1$ is des-Xaa or Ala; Xaa$_2$ is Tyr, D-Tyr or des-Xaa or Gly; Xaa$_5$ is des-Xaa or Asn; Xaa$_8$ is an amino acid residue selected from the group consisting of D-Trp and substituted D-Ala wherein the β-carbon is substituted by a carbocyclic aryl-containing radical or by a saturated carbocyclic radical; Xaa$_9$ is (C)aminomethyl Phe with C being H or lower alkyl; and Xaa$_{13}$ is Ser or D-Ser.

3. A peptide according to claim 2 wherein Xaa$_8$ is (A)D-Trp, (B)D-Ala, or (B)D,L-Ala where A is H, Cl, F, Br, NO$_2$ or formyl and B is naphthyl, fluorenyl, adamantyl, anthryl, biphenyl, tri(lower alkyl)phenyl, pentamethylphenyl, phenanthryl, trialkylcyclohexyl, perhydronaphthyl or perhydrobiphenyl.

4. A peptide according to claim 3 wherein Xaa$_1$, Xaa$_2$ and Xaa$_5$ are des-Xaa and C is methyl, ethyl, isopropyl or isobutyl.

5. A peptide according to claim 3 wherein Xaa$_9$ is (isopropylaminomethyl)Phe, i.e. IAmp.

6. A peptide according to claim 5 wherein Xaa$_{13}$ is D-Ser.

7. A peptide according to claim 5 wherein Xaa$_2$ is Tyr or D-Tyr.

8. A peptide according to claim 5 wherein D-Xaa$_8$ is (A)Trp and A is H or F.

9. A peptide according to claim 5 wherein D-Xaa$_8$ is (B)D-Ala or (B)D,L-Ala and B is 3-(1-naphthyl).

10. A peptide according to claim 5 wherein D-Xaa$_8$ is (B)D-Ala or (B)D,L-Ala and B is 3-(9-fluorenyl).

11. A peptide according to claim 5 wherein D-Xaa$_8$ is (B)D-Ala or (B)D,L-Ala and B is 3-(1-adamantyl).

12. A peptide according to claim 5 wherein D-Xaa$_8$ is (B)D-Ala or (B)D,L-Ala and B is 3-(4-biphenyl).

13. A peptide according to claim 5 wherein D-Xaa$_8$ is (B)D-Ala or (B)D,L-Ala and B is 3-(2-anthryl).

14. A peptide according to claim 5 wherein D-Xaa$_8$ is (B)D-Ala or (B)D,L-Ala and B is 3-(2,4,6-trimethylphenyl).

15. A peptide according to claim 1 having the amino acid sequence:

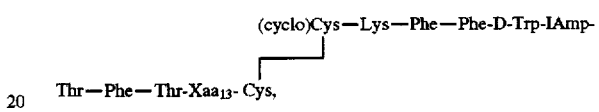

wherein Xaa$_{13}$ is Ser or D-Ser.

16. A pharmaceutical composition comprising a mixture of a peptide according to claim 1 and at least one pharmaceutically acceptable carrier.

17. A method of arresting tumor growth in a patient, which method comprises administering an effective amount of a composition according to claim 16, which amount is effective to at least slow the growth of a tumor having SSTR1 receptors.

18. A cyclic somatostatin (SRIF) analog peptide according to claim 2 having the amino acid sequence:

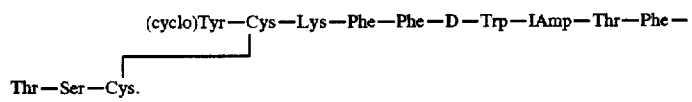

19. The peptide of claim 18 wherein Tyr is iodinated.

20. A cyclic somatostatin (SRIF) analog peptide having specific affinity for the SRIF receptor SSTR1, which peptide has an amino acid sequence at least 8 residues in length, contains a Cys-Cys disulfide bond with a sequence of at least 6 residues located between said Cys residues as a ring, and contains, centrally of said at least 6-residue sequence, an amino acid residue selected from the group consisting of D-Trp and substituted D-Ala wherein the β-carbon is substituted by a carbocyclic aryl-containing radical or by a saturated carbocyclic radical, which analog peptide is characterized by the presence of (C)Amp joined immediately C-terminally to said amino acid residue, with C being H or lower alkyl.

21. A peptide according to claim 20 wherein C is lower alkyl.

* * * * *